United States Patent
Bundock et al.

(10) Patent No.: US 11,008,579 B2
(45) Date of Patent: *May 18, 2021

(54) MUTAGENESIS METHOD USING POLYETHYLENE GLYCOL MEDIATED INTRODUCTION OF MUTAGENIC NUCLEOBASES INTO PLANT PROTOPLASTS

(71) Applicant: Keygene N.V., Wageningen (NL)

(72) Inventors: Paul Bundock, Amsterdam (NL); Michiel Theodoor Jan De Both, Wageningen (NL); Frank Lhuissier, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/084,935

(22) Filed: Mar. 30, 2016

(65) Prior Publication Data

US 2016/0201071 A1  Jul. 14, 2016

Related U.S. Application Data

(63) Continuation of application No. 13/551,143, filed on Jul. 17, 2012, now Pat. No. 9,365,860, which is a continuation of application No. 12/809,384, filed as application No. PCT/NL2007/000326 on Dec. 21, 2007, now abandoned.

(51) Int. Cl.
*C12N 15/82* (2006.01)

(52) U.S. Cl.
CPC ..... *C12N 15/8206* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 6,824,983 B1 | 11/2004 | Rak et al. | |
| 9,365,860 B2* | 6/2016 | Bundock | C12N 15/8206 |
| 2004/0014057 A1 | 1/2004 | Kmiec et al. | |
| 2004/0029275 A1* | 2/2004 | Brown | C12N 15/111 |
| | | | 435/375 |
| 2005/0074801 A1 | 4/2005 | Monia et al. | |
| 2006/0162024 A1 | 7/2006 | Beetham et al. | |
| 2007/0141134 A1 | 6/2007 | Kosak | |
| 2009/0205064 A1 | 8/2009 | Schopke et al. | |
| 2009/0307805 A1 | 12/2009 | De Both et al. | |
| 2010/0055780 A1 | 3/2010 | Bundock et al. | |
| 2010/0186124 A1 | 7/2010 | Bundock et al. | |
| 2010/0223691 A1 | 9/2010 | Bundock | |
| 2011/0258711 A1 | 10/2011 | Rouppe Van Der Voort et al. | |
| 2011/0312094 A1 | 12/2011 | Bundock | |

FOREIGN PATENT DOCUMENTS

| | | |
|---|---|---|
| DE | 10242531 A1 | 3/2004 |
| JP | 2007/167011 A | 5/2007 |
| WO | WO 01/25460 A2 | 4/2001 |
| WO | WO 01/38509 A | 5/2001 |
| WO | WO 01/87914 A | 11/2001 |
| WO | WO 2001/094610 A2 | 12/2001 |
| WO | WO 2007/012138 A1 | 2/2007 |
| WO | WO 2007/037676 A | 4/2007 |
| WO | WO 2007/073154 A | 6/2007 |
| WO | WO 2007/073166 A | 6/2007 |
| WO | WO 2007/073170 A1 | 6/2007 |
| WO | WO 2009/046334 A1 | 4/2009 |
| WO | WO 2009/046334 A4 | 4/2009 |

OTHER PUBLICATIONS

Etoki Shokubutsu Soshiki Biaya; Introduction to Plant Tissue Culture by Illustration, Ohmsha Co., Ltd., 1992.
Shokubutsu Protopurasuto No Saibo Kogaku; Cellular Engineering of the Plant Protoplast, Kodansha Co., Ltd., 1993.
Bilang et al., Single-Stranded DNA as a Recombination Substrate in Plants as Assessed by Stable and Transient Recombination Assay, Molec. and Cell. Biol. (1992) 12: 329-336.
Gamper H.B. et al., The DNA Strand of Chimeric RNA/DNA Oligonucleotides Can Direct Gene Repair/Conversion Activity in Mammalian and Plant Cell-Free Extracts, Nuc. Acid Res. (2000) 28: 4332-4339.
Kao, K.N., et al., "A Method for High-frequency Integeneric Fusion of Plant Protoplasts", Planta (Berl.), (1974) 115: 355-367.
Parekh-Olmedo, H., et al., "Targeted Nucleotide Exchange in *Saccharomyces cerevisiae* Directed by Short Oligonucleotides Containing Locked Nucleic Acids", Chemistry & Biology, (2002) vol. 9, pp. 1073-1084.
Dong, C., et al., "Oligonucleotide-Directed Gene Repair in Wheat Using a Transient Plasmid Gene Repair Assay System", Plant Cell Rep., (2006) vol. 25, pp. 457-465.
Beetham, P.R. et al., "A Tool for Functional Plant Genomics: Chimeric RNA/DNA Oligonucleotides Cause In Vivo Gene-Specific Mutations", Proc. Natl. Acad. Sci. USA, (1999) vol. 96, pp. 8774-8778.

(Continued)

Primary Examiner — Brent T Page
(74) Attorney, Agent, or Firm — Finnegan, Henderson, Farabow, Garrett and Dunner LLP

(57) ABSTRACT

Method for targeted alteration of a duplex acceptor DNA sequence in a plant cell protoplast, comprising combining the duplex acceptor DNA sequence with a donor mutagenic nucleobase, wherein the duplex acceptor DNA sequence contains a first DNA sequence and a second DNA sequence which is the complement of the first DNA sequence and wherein the donor mutagenic nucleobase comprises at least one mismatch with respect to the duplex acceptor DNA sequence to be altered, preferably with respect to the first DNA sequence, wherein the method further comprises a step of introducing the donor mutagenic nucleobase into the cell protoplasts using polyethylene glycol (PEG) mediated transformation and the use of PEG protoplast transformation for enhancing the rate of targeted mutagenesis.

10 Claims, No Drawings

Specification includes a Sequence Listing.

(56) References Cited

OTHER PUBLICATIONS

Zhu, T. et al., "Targeted Manipulation of Maize Genes In Vivo Using Chimeric RNA/DNA Oligonucleotides", Proc. Natl. Acad. Sci. USA, (1999) vol. 96, pp. 8768-8773.
Appeal Case No. 2013-16142, "Written Inquiry", Pat. Appln. No. 2010-539319, mailed on Jun. 11, 2014. (In Japanese).
"Introduction to Explanation by a Picture Plant Tissue Culture," Ohmsha, Ltd., (1992), pp. 119-121. (CD8) (Cited Document 6 in the Appeal Case No. 2013-16142, Written Inquiry, Pat. Appln. No. 2010-539319, mailed on Jun. 11, 2014).
"Cellular Engineering of the Plant Protoplast," Kodansha Ltd., (1993), pp. 98-105. (CD9) (Cited Document 8 in the Appeal Case No. 2013-15142, Written Inquiry, Pat. Appln. No. 2010-539319, mailed on Jun. 11, 2014).
Datta, S.K. et al., "Herbicide-Resistant Indica Rice Plants From IRRI Breeding Line IR72 After PEG-Mediated Transformation of Protoplasts," Plant Molecular Biology (1992) 20: 619-629.
Gharti-Chhetri, G.B. et al., "Polyethylene Glycol-Mediated Direct Gene Transfer in *Nicotiana* Spp.," Physloiogla Plantarum (1992) 85: 345-351.
Mathur, J., and Koncz, C., "PEG-Mediated Protoplast Transformation with Naked DNA," Methods in Molecular Biology, vol. 82: *Arabidopsis* Protocols (1998), Humana Press Inc., Totowa, NJ, 267-276.
Notice of Opposition against European Patent No. 1223799 filed by Keygene NV in the European Patent Office dated Sep. 1, 2010 (33 pages).
Brücker et al. Target Site-Directed Mutagenesis of a Heme Oxygenase Locus by Gene Replacement in the Moss Ceratodon Purpureus, (2005) Planta 220: 864-874.
Lazzeri P.A. et al., Stable Transformation of Barley via PEG-Induced Direct DNA Uptake into Protoplasts, (1991) Theor Appl. Genet. 81: 437-444.
The International Search Report received in the corresponding International Patent Application No. PCT/NL2007/000326, dated Oct. 6, 2008.
The International Report on Patentability received in the corresponding International Patent Application No. PCT/NL2007/000326, dated Feb. 10, 2010.
Hohe et al., "An improved and highly standardized transformation procedure allows efficient production of single and multiple targeted gene-knockouts in a moss. *Physcomitrella patens*", Current Genetics (2004) 44(6): 339-347.
Chan P.P. et al., Targeted Correction of an Episomal Gene in Mammalian Cells by a Short DNA Fragment Tethered to a Triplex-Forming Oligonucleotide, J. Biol. Chem. (1999) 274(17): 11541-46.
Potrykus I., Gene Transfer to Cereals: An Assessment, Nature Biotech. (1990) 8: 535-42.
Lipofectin® manual (https://www.thermofisher.com/us/en/home/life-science/cell-culture/transfection/transfection-support/transfection-reagent-faqs.html#faq17).
Non-final Office Action issued in U.S. Appl. No. 12/809,384 dated Jan. 18, 2012.
Non-final Office Action issued in U.S. Appl. No. 13/551,143 dated Sep. 4, 2012.
Final Office Action issued in U.S. Appl. No. 13/551,143 dated Mar. 5, 2013.
Non-final Office Action issued in U.S. Appl. No. 13/551,143 dated Feb. 11, 2015.
Final Office Action issued in U.S. Appl. No. 13/551,143 dated Oct. 27, 2015.
Jeon, J. et al. "Efficient Transient expression and Transformation of PEG-Mediated Gene Uptake Into Mesophyll Protoplasts of Pepper (*Capsicum annuum* L.)," Plant Cell Tiss Organ Cult, 88:225-232 (2007).

* cited by examiner

SEQUENCE LISTING

<160> NUMBER OF SEQ ID NOS: 5

<210> SEQ ID NO 1
<211> LENGTH: 40
<212> TYPE: DNA
<213> ORGANISM: artificial
<220> FEATURE:
<223> OTHER INFORMATION: Oligonucleotide for Targeted Nucleotide
      exchange

<400> SEQUENCE: 1
tcagtaccta tcatcctacg tggcacttga cctgttatag                           40

<210> SEQ ID NO 2
<211> LENGTH: 40
<212> TYPE: DNA
<213> ORGANISM: artificial
<220> FEATURE:
<223> OTHER INFORMATION: oligonucletide for targeted nucleotide exchange

<400> SEQUENCE: 2
tcagtaccta tcatcctacg ttgcacttga cctgttatag                           40

<210> SEQ ID NO 3
<211> LENGTH: 40
<212> TYPE: DNA
<213> ORGANISM: artificial
<220> FEATURE:
<223> OTHER INFORMATION: oligonucleotide for targeted nucleotide
      exchange

<400> SEQUENCE: 3
atcgatcgat cgatcgatcg atcgatcgat cgatcgatcg                           40

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
ggtcaagtgc cacgtaggat                                                 20

<210> SEQ ID NO 5
<211> LENGTH: 20
<212> TYPE: DNA

```
<213> ORGANISM: artificial
<220> FEATURE:
<223> OTHER INFORMATION: primer

<400> SEQUENCE: 5
gggtgcttca ctttctgctc                                                    20
```

MUTAGENESIS METHOD USING POLYETHYLENE GLYCOL MEDIATED INTRODUCTION OF MUTAGENIC NUCLEOBASES INTO PLANT PROTOPLASTS

CROSS-REFERENCE TO RELATED PATENT APPLICATIONS

This application is a continuation of application Ser. No. 13/551,143, filed Jul. 17, 2012, which is a continuation of application Ser. No. 12/809,384 (now abandoned), with a § 371(c) date of Jun. 30, 2010, which is a national stage filing under 35 U.S.C. § 371 of PCT/NL2007/000326, filed Dec. 21, 2007. All of these applications are incorporated herein by reference in theft entirety.

FIELD OF THE INVENTION

The present invention relates to a method for the specific and selective alteration of a nucleotide sequence at a specific site of the DNA in a target cell by the introduction into the cell of a single stranded DNA oligonucleotide mutagenic nucleobase. More in particular, the invention relates to a process of targeted mutagenesis by the introduction of a mutagenic nucleobase into plant protoplasts using polyethylene glycol (PEG). The invention further relates to kits containing a mutagenic nucleobase and PEG. The invention also relates to the use of PEG for enhancing targeted mutagenesis.

BACKGROUND OF THE INVENTION

The process of deliberately creating changes in the genetic material of living cells has the goal of modifying one or more genetically encoded biological properties of that cell, or of the organism of which the cell forms part or into which it can regenerate. These changes can take the form of deletion of parts of the genetic material, addition of exogenous genetic material, or changes in the existing nucleotide sequence of the genetic material. Methods of altering the genetic material of eukaryotic organisms have been known for over 20 years, and have found widespread application in plant, human and animal cells and micro-organisms for improvements in the fields of agriculture, human health, food quality and environmental protection. The most common methods consist of adding exogenous DNA fragments to the genome of a cell, which will then confer a new property to that cell or its organism over and above the properties encoded by already existing genes (including applications in which the expression of existing genes will thereby be suppressed). Although many such examples are effective in obtaining the desired properties, these methods are nevertheless not very precise, because there is no control over the genomic positions in which the exogenous DNA fragments are inserted (and hence over the ultimate levels of expression), and because the desired effect will have to manifest itself over the natural properties encoded by the original and well-balanced genome. On the contrary, methods of targeted mutagenesis that will result in the addition, deletion or conversion of nucleotides in predefined genomic loci will allow the precise modification of existing genes. In addition, due to the precise nature of targeted mutagenesis, its is expected that novel plant lines obtained in this way will be more readily accepted by consumers.

Targeted mutagenesis is a site-directed mutagenesis method that is based on the delivery into the eukaryotic cell nucleus of synthetic mutagenic nucleobases (molecules consisting of short stretches of nucleotide-like moieties that resemble DNA in their Watson-Crick basepairing properties, but may be chemically different from DNA) (Alexeev and Yoon, Nature Biotechnol. 16: 1343, 1998; Rice, Nature Biotechnol. 19: 321, 2001; Kmiec, J. Clin. Invest. 112: 632, 2003). Once introduced into the cell, such mutagenic nucleobases basepair with the complementary sequence at the target locus. By deliberately designing a mismatch in the nucleobase, the mismatch may a nucleotide conversion at the corresponding position in the target genomic sequence. This method allows the conversion of single or at most a few nucleotides in endogenous loci, but may be applied to create stop codons in existing loci, resulting in a disruption of their function, or to create codon changes, resulting in genes encoding proteins with altered amino acid composition (protein engineering).

Targeted mutagenesis has been described in plant, animal and yeast cells. Two different classes of synthetic mutagenic nucleobases have been used in these studies, the chimeric DNA:RNA nucleobases or single stranded nucleobases.

The chimeric DNA:RNA nucleobases (chimeras) are self complementary molecules consisting of a 25 bp DNA only region and a 25 bp complementary sequence made up of 5 bp of core region of DNA flanked on either side by 10 bp of 2'-O-methylated RNA that are thought to aid stability of the chimera in the cell. The 5 bp core region includes in its centre an engineered mismatch with the nucleotide to be altered in the genomic target DNA sequence. Both these regions are linked by 4 bp thymidine hairpins. Upon introduction into the cell the chimera is thought form a double D-loop with its target sequence and a mismatch is formed between the chimera and the target nucleotide. This mismatch is then resolved by endogenous cellular DNA repair proteins by conversion of the genomic nucleotide. The first examples of targeted mutagenesis using chimeras came from animal cells (reviewed in Igoucheva et al. 2001 *Gene Therapy* 8, 391-399) and were then also later used to achieve targeted mutagenesis in plant cells (Beetham et al. 1999 *Proc. Natl. Acad. Sci. USA* 96: 8774-8778; Zhu et al. 1999 *Proc. Natl. Acad. Sci. USA* 96, 8768-8773; Zhu et al. 2000 *Nature Biotech.* 18, 555-558; Kochevenko et al. 2003 *Plant Phys.* 132: 174-184; Okuzaki et al. 2004 *Plant Cell Rep.* 22: 509-512). Unlike human cells, a plant cell in which a targeted mutagenesis event has occurred can be regenerated into an intact plant and the mutation transferred to the next generation, making it an ideal tool for both research and commercial mutagenesis of important food crops. However, extensive research by many laboratories has shown that the targeted mutagenesis frequency using chimeras is quite low and variable, or not even detectable (Ruiter et al. 2003 *Plant Mol. Biol.* 53, 715-729, Van der Steege et al. (2001) *Nature Biotech.* 19: 305-306), and depended on such factors as the transcriptional status of the target, the position of the cell in the cell cycle, the sequence of the target and the quality of the chimeras, which are difficult to synthesize. Due to the relatively low frequency of targeted mutagenesis with the methods known in the art, such events can only be detected when alteration of a single nucleotide of the genomic target results in a dominant selectable phenotype. In plant cells specific point mutations were introduced into the open reading frame of the acetolactate synthase (ALS, in maize AHAS) gene which catalyzes the initial step common to the synthesis of the branched chain amino acids leucine, isoleucine and valine. In tobacco, single nucleotide alterations are sufficient to produce the codon conversions P194Q or W571L. The ALS protein produced after either of these codon conversions is insensitive to inhibition by the sulfonylurea class of herbicides, thus providing a method of selection for single nucleotide conversions at a chromosomal locus.

Due to the difficulties of working with chimeras, more reliable alternative oligonucleotide designs have been sought. Several laboratories have investigated the ability of single stranded (ss) nucleobases to perform targeted mutagenesis. These have been found to give more reproducible results, be simpler to synthesize, and can also include modified nucleotides to improve the performance of the mutagenic nucleobase in the cell (Liu et al. 2002 *Nucl. Acids Res.* 30: 2742-2750; review, Parekh-Olmedo et al. 2005 *Gene Therapy* 12: 639-646; Dong et al. 2006 *Plant Cell Rep.* 25: 457-65; De Piédoue et al. 2007 *Oligonucleotides* 17: 258-263).

Targeted mutagenesis has been described in a variety of patent applications of Kmiec, inter alia in WO0173002, WO03/027265, WO01/87914, WO99/58702, WO97/48714, WO02/10364. In WO 01/73002 it is contemplated that the low efficiency of gene alteration obtained using unmodified nucleobases is largely believed to be the result of their degradation by nucleases present in the reaction mixture or the target cell. To remedy this problem, it is proposed to incorporate modified nucleotides that render the resulting nucleobases resistant against nucleases. Typical examples of such modified nucleotides include phosphorothioate linkages or 2'-O-methyl-analogs. These modifications are preferably located at the ends of the nucleobase, leaving a central unmodified domain surrounding the targeted base. In support of this, patent application WO 02/26967 shows that certain modified nucleotides increasing the intracellular lifetime of the nucleobase enhance the efficiency of targeted mutagenesis in an in vitro test system and also at a mammalian chromosomal target. Not only the nuclease resistance, but also the binding affinity of an ss mutagenic nucleobase to its complementary target DNA has the potential to enhance the frequency of targeted mutagenesis dramatically. A ss nucleobase containing modified nucleotides that enhance its binding affinity may more efficiently find its complementary target in a complex genome and/or remain bound to its target for longer and be less likely to be removed by proteins regulating DNA transcription and replication. An in vitro targeted mutagenesis assay has been used to test many modified nucleotides to improve the efficiency of the mutagenesis process. Locked nucleic acids (LNA) and C5-propyne pyrimidines have modifications of the sugar moiety and base respectively that stabilize duplex formation and raise the melting temperature of the duplex. When these modified nucleotides are incorporated on an ss nucleobase, they enhance the efficiency of targeted mutagenesis up to 13 fold above that obtained using an unmodified nucleobase of the same sequence. See in his respect WO2007073166 and WO2007073170 in the name of the present applicants.

The present inventors have set out to improve the frequency of targeted mutagenesis in plant cells by optimizing the method used to introduce the mutagenic nucleobases into plant cells. The most widely used method for transformation of plant cells, *Agrobacterium* mediated transformation, transfers a section of its tumour inducing (Ti) plasmid, the so-called T-DNA, to plant cells where it efficiently integrates into the plant genome at a random position. The T-DNA is flanked at either end by "border" sequences of up to 22 bps derived from the Ti plasmid which share no homology with the target sequence. Given the short length of the ss mutagenic nucleobases used for targeted mutagenesis, the border sequences would interfere with the process. Thus, targeted mutagenesis can only be achieved in plant cells through direct DNA transfer using chemical or physical methods.

In the literature, several such direct DNA transfer techniques have been reported and include electroporation, polyethylene glycol (PEG) treatment of protoplasts, biolistic bombardment of plant callus material and microinjection of DNA into individual protoplasts or tissue. The art provides no indication as regards a preferred method for the transfer of ss nucleobases for targeted mutagenesis, in particular for DNA transfer to plants or plant protoplasts.

In order to achieve as high a targeted mutagenesis efficiency in plants as possible, the present inventors in the course of their investigations have identified four factors that are to be optimized. First, the mutagenic nucleobase is preferably introduced with a high transformation efficiency, i.e. introduced into as many plant cells as possible. Second, the treatment is preferably not lethal to most of the cells, ensuring that as many cells as possible that are transformed also survive the transformation procedure (survival efficiency). Thirdly, the transformation method is preferably not detrimental to the subsequent divisions of the transformed plant cells to form microcalli (regeneration/plating efficiency) and finally it is preferably possible to identify individual regenerated plants derived from targeted mutagenesis events without application of a selection (identification efficiency).

Most methods for transformation of DNA to individual plant cells use protoplasts, derived directly from leaves (mesophyll protoplasts) or from cell suspensions (reviewed in Sheen, J. (2001) *Plant Phys.* 127: 1466-1475). Protoplasts can be used for transient expression studies, in which case gene expression or protein localization can be assessed shortly after transformation, or for production of stably transformed plants when the protoplasts are grown on medium to promote callus formation and organogenesis.

Transformation of plant protoplasts using electroporation has been previously reported (Fromm et al. (1985) *Proc. Natl. Acad. Sci. USA* 82: 5824-5828; Nishiguchi et al. (1986) *Plant Cell Rep.* 5: 57-60; Ou-Lee et al. (1986) *Proc. Natl. Acad. Sci. USA* 83: 6815-6819; Hauptmann et al. (1987) *Plant Cell Rep.* 6: 265-270; Jones et al. (1989) *Plant Mol. Biol.* 13: 503-511). Generally, the field strength (V/cm) giving the highest transformation efficiency results in <50% of protoplast survival (Jones et al. (1989) *Plant Mol. Biol.* 13: 503-511). In tobacco electroporation studies we have found that only approximately 10% of the total tobacco protoplasts in the sample are transformed with a plasmid expressing GFP and this relatively low transformation efficiency has also been observed after electroporation of *Arabidopsis* protoplasts (Miao et al. (2007) *Nature Protocols* 10: 2348-2353). In general, the optimal electroporation conditions must be determined empirically for each plant species and these can also vary according to the type of electroporation machine and the method and buffers used for protoplast isolation. While electroporation has been successfully applied to many plant species, it remains a difficult technique with several serious limitations (as discussed in: http://genetics.mgh.harvard.edu/sheenweb/faq.html), in particular in terms of reproducibility. Hence electroporation is less desirable for enhancing the overall efficiency for TNE of targeted mutagenesis.

Direct gene transfer using biolistic delivery has been very successful in generating transgenic crop plants and is routinely used for the stable integration of transgenes. Cell suspensions are transferred to solid medium for callus induction and this material is bombarded by gold particles driven by a high pressure gas source. It has been reported that the transformation frequencies are low, ~0.01% of the total cells are transformed. Due to the low transformation efficiency, the survival of the transformed cells is difficult to assess. In contrast, the regeneration efficiency after bombardment is likely to be high due to the strongly dividing material that is treated. However, as TNE will occur in a single cell of a single callus, such an event will be easily lost if it is not selected for or, alternatively, regenerated plants will be chimeric for the targeted mutagenesis event. Thus, bombardment is not practical for performing targeted mutagenesis at non-selectable loci. In contrast, it is possible to recover targeted mutagenesis events using protoplasts as each microcallus is derived from a single protoplast.

Induced single nucleotide conversions by chimeras at ALS have demonstrated that targeted mutagenesis can be detected in tobacco, maize and rice cells. Bombardment has been used for tobacco (Beetham et al. 1999 *Proc. Natl. Acad. Sci. USA* 96: 8774-8778; Kochevenko et al. 2003 *Plant Phys.* 132: 174-184), maize (Zhu et al. 1999 *Proc. Natl. Acad. Sci. USA* 96, 8768-8773) and rice (Okuzaki et al. 2004 *Plant Cell Rep.* 22: 509-512). Beetham et al. (1999) reported that the frequency of herbicide resistance after direct transfer of chimeras increased 20 fold compared to the background mutation rate (assumed to be $10^{-7}$ to $10^{-8}$). Kochevenko et al. have also used electroporation to perform targeted mutagenesis experiments in tobacco mesophyll protoplasts. The present inventors were able to obtain herbicide resistant tobacco callus at a frequency of 0.0001%, comparable to the frequency obtained by Beetham et al. This suggests that when dealing with the same plant species and the same target nucleotide that in this case the direct DNA delivery method does not have a large impact on the targeted mutagenesis efficiency, which remains at an undesirable low level. However, Ruiter et al. (2003 *Plant Mol. Biol.* 53, 715-729) performed both bombardment and electroporation experiments in both tobacco and oil seed rape, and could not detect any effect of the chimeras.

Bombardment of both maize and rice callus has been reported at an efficiency of 0.01% of the cells that are transformed (Zhu et al. (1999) *Proc. Natl. Acad. Sci. USA* 96, 8768-8773; Okuzaki et al. (2004 (*Plant Cell Rep.* 22: 509-512). However, this is only feasible at selectable loci.

PEG-mediated protoplast transformation in itself has been known already since 1985. The first method for protoplast transformation utilized PEG (Krens et al. (1982) *Nature* 296: 72-74; Potyrykus et al. (1985) *Plant Mol. Biol. Rep.* 3:117-128; Negrutiu et al. (1987) *Plant Mol. Biol.* 8: 363-373). The technique is applicable to protoplasts from many different plants (Rasmussen et al. (1993) *Plant Sci.* 89: 199-207). PEG is thought to stimulate transformation by precipitating the DNA, in the presence of divalent cations, onto the surface of the protoplasts from where it then becomes internalized (Maas & Werr (1989) *Plant Cell Rep.* 8: 148-151). PEG transformation is the method of choice for transformation of *Arabidopsis* protoplasts (http://genetics.mgh.harvard.edu/sheenweb/faq.html) (Mathur et al. Methods in molecular biology, vol. 82, 267-276) and conforms well to the four requirements defined for a transformation method for efficient TNE. When tobacco protoplasts are treated with PEG, a biotin-labelled ss oligonucleotide can be detected in all cells examined. Survival, as assessed by vital staining using fluorescein diacetate, is >90% after PEG treatment. Not all protoplasts retain the ability to divide and form microcalli. In a typical isolation of non-treated tobacco protoplasts, approximately 25% form microcalli. PEG treatment does have a slight impact on regeneration efficiency, which drops to approximately 10%, but this is not dramatic compared to other transformation methods. None of the above describe prior art has contemplated the use of PEG transformation for site-directed mutagenesis, in particular TNE.

The present inventors have set out to improve the method of direct DNA transfer to obtain efficient targeted mutagenesis in plant cells. The present inventors have found that from amongst the transformation technologies as described herein elsewhere, PEG protoplast transformation enhances the overall targeted mutagenesis efficiency significantly compared to electroporation and biolistics. This is surprising, as the technologies for targeted mutagenesis in plants to date appeared to favour electroporation with the associated low efficiencies. Furthermore most improvements in the technology were directed at improving the mutagenic nucleobases and not in the delivery system for delivering the mutagenic nucleobase to the genomic target DNA.

For sake of comparison, the present inventors used ss mutagenic nucleobase designed to produce a P194Q conversion at the ALS locus leading to herbicide resistance. Identical ss mutagenic nucleobases were introduced into tobacco mesophyll protoplasts using either PEG mediated transformation or electroporation and herbicide resistant cells were selected using identical selection conditions. Thus the present inventors have found that PEG-mediated transformation of plant cells is the most efficient method to perform targeted mutagenesis in plant cells compared to known methods of transformation.

In one aspect the invention pertains to a method for targeted alteration of a duplex acceptor DNA sequence in a plant cell protoplast, comprising combining the duplex acceptor DNA sequence with a ss mutagenic nucleobase, wherein the duplex acceptor DNA sequence contains a first DNA sequence and a second DNA sequence which is the complement of the first DNA sequence and wherein the donor ss mutagenic nucleobase comprises at least one mismatch with respect to the duplex acceptor DNA sequence to be altered, preferably with respect to the first DNA sequence, wherein the method further comprises a step of introducing the ss mutagenic nucleobase into the cell protoplasts using polyethylene glycol (PEG) mediated transformation.

The ss mutagenic nucleobase is brought into contact with protoplasts of the plant to be transformed using a PEG transformation based technology. The PEG mediated transformation technology in itself is widely known and were necessary, small amendments to particular protocols can be made by the skilled man without departing from the gist of the present invention.

The ss mutagenic nucleobase used in the present invention have a length that is in line with other (chimeric) ss mutagenic nucleobase used in targeted mutagenesis, i.e. typically between 10-60 nucleotides, preferably 20-55 nucleotides, more preferably 25-50 nucleotides. In certain embodiments of the invention, the ss mutagenic nucleobase used in the present invention the can be modified, for instance by LNA and/or propynyl modifications as described in applicant's WO2007073166 and WO2007073170. Thus in certain embodiments, the ss mutagenic nucleobase contains at least one LNA located at a position that is from the targeted mismatch and preferably two LNAs located at least one nucleotide removed from either side of the mismatch and. Furthermore, these LNAs are at least 3, 4 or 5 nucleotides removed form the 5' and/or 3' ends of the ss mutagenic nucleobase. In certain embodiments, the ss mutagenic nucleobase can comprise one or more propyne substitutions, essentially as described in WO2007073166 and WO2007073170. In certain embodiments, the donor ss mutagenic nucleobase may be conjugated to protein such as a nuclear localisation signal. In this embodiment, the oligonucleotide used in the present invention is coupled via conventional (linker) technology to a nuclear localisation signal such as the known (NLS) peptide of the SV40 large T antigen, GATA transcription factor 11, DNA repair helicase XBP1, Light mediated protein DET1, ERF transcription factor, PR-related transcript activator PTI6 and nuclear coiled protein, essentially as described in applicants copending application PCT/NL2007/000279. The oligonucleotide-nuclear localisation signal conjugate can be used in the PEG-based transformation methodology described herein.

The alteration produced by the method of the present invention is a deletion, a substitution or an insertion of at least one nucleotide. Preferably the alteration is a substitution. More nucleotides may be altered in one oligonucleotide, but it is expected that efficiency will diminish, hence there is a preference for altering one nucleotide.

The target DNA (or duplex acceptor DNA) can be from any source, but preferably the target DNA is from a plant. Preferably the target DNA is from genomic DNA, linear DNA, artificial chromosomes, nuclear chromosomal DNA, organelle chromosomal DNA, episomal DNA. The method according to the invention can be used for altering a cell, correcting a mutation by restoration to wild type, inducing a mutation, inactivating an enzyme by disruption of coding region, modifying bioactivity of an enzyme by altering coding region, modifying a protein by disrupting the coding region.

In one aspect the invention relates to the use of PEG mediated transformation for enhancing the efficiency of targeted mutagenesis in plant protoplasts.

Without being bound by theory, it is thought that the use of PEG mediated transformation precipitates the DNA on the cell membrane of the protoplast. The precipitated DNA is encapsulated by the cell membrane and introduced into the protoplast in a shielded form.

The protoplast will, in the course of its normal cell cycle, directly after its formation by removal of the cell wall, start its normal cell wall regeneration process. The cell division typically starts later (from several hours up to a few days). The targeted nucleotide exchange generally takes place during the cell division, using the cell's repair mechanism. In the time period between the introduction of the donor DNA in the protoplast and the start of the cell division, the donor DNA is prone to attack form the cells defence mechanism such as exonucleases and is likely to be degenerated and hence become ineffective for TNE. With the use of PEG-mediated transformation technology, the donor DNA is encapsulated via endocytosis and is in this way at least temporarily shielded from the degenerative action of endonucleases. When the DNA is released from its encapsulated form, it has an increased chance of being present at or around the moment of the cell division, during which the DNA (i.e. the ss mutagenic nucleobase) is available to find its complement in the DNA of the acceptor cell and exchange the nucleotide as in common targeted mutagenesis mechanisms.

EXAMPLES

Comparison of Targeted Mutagenesis Frequencies Using Either PEG Mediated Transformation or Electroporation Protoplast Isolation In vitro shoot cultures of Nicotiana tabacum cv Petit Havana line SR1 are maintained on MS20 medium with 0.8% Difco agar in high glass jars at 16/8 h photoperiod of 2000 lux at 25° C. and 60-70% RH. MS20 medium is basic Murashige and Skoog's medium (Murashige, T. and Skoog, F., *Physiologia Plantarum*, 15: 473-497, 1962) containing 2% (w/v) sucrose, no added hormones and 0.8% Difco agar. Fully expanded leaves of 3-6 week old shoot cultures are harvested. The leaves are sliced into 1 mm thin strips, which are then transferred to large (100 mm×100 mm) Petri dishes containing 45 ml MDE basal medium for a preplasmolysis treatment of 30 min. MDE basal medium contained 0.25 g KCl, 1.0 g $MgSO_4.7H_2O$, 0.136 g of $KH_2PO_4$, 2.5 g polyvinylpyrrolidone (MW 10,000), 6 mg naphthalene acetic acid and 2 mg 6-benzylaminopurine in a total volume of 900 ml. The osmolality of the solution is adjusted to 600 mOsm·$kg^{-1}$ with sorbitol, the pH to 5.7. 5 mL of enzyme stock SR1 are then added. The enzyme stock consists of 750 mg Cellulase Onozuka R10, 500 mg driselase and 250 mg macerozyme R10 per 100 ml, filtered over Whatman paper and filter-sterilized. Digestion is allowed to proceed overnight in the dark at 25° C. The digested leaves are filtered through 50 µm nylon sieves into a sterile beaker. An equal volume of cold KCl wash medium is used to wash the sieve and pooled with the protoplast suspension. KCl wash medium consisted of 2.0 g $CaCl_2.2H_2O$ per liter and a sufficient quantity of KCl to bring the osmolality to 540 mOsm·$kg^{-1}$. The suspension is transferred to 10 mL tubes and protoplasts are pelleted for 10 min at 85×g at 4° C. The supernatant is discarded and the protoplast pellets carefully resuspended into 5 mL cold MLm wash medium, which is the macro-nutrients of MS medium (Murashige, T. and Skoog, F., *Physiologia Plantarum*, 15: 473-497, 1962) at half the normal concentration, 2.2 g of $CaCl_2.2H_2O$ per liter and a quantity of mannitol to bring the osmolality to 540 mOsm·$kg^{-1}$. The content of 2 tubes is combined and centrifuged for 10 min at 85×g at 4° C. The supernatant is discarded and the protoplast pellets carefully resuspended into 5 mL cold MLs wash medium which is MLm medium with mannitol replaced by sucrose.

The content of 2 tubes is pooled and 1 mL of KCl wash medium added above the sucrose solution care being taken not to disturb the lower phase. Protoplasts are centrifuged for 10 min at 85×g at 4° C. The interphase between the sucrose and the KCl solutions containing the live protoplasts is carefully collected. An equal volume of KCl wash medium is added and carefully mixed. The protoplast density is measured with a haemocytometer.

PEG Transformation

The protoplast suspension is centrifuged at 85×g for 10 minutes at 5° C. The supernatant is discarded and the protoplast pellet resuspended to a final concentration of $10^6.ml^{-1}$ in KCl wash medium. In a 10 mL tube, 250 µL of protoplast suspension, 1.6 nmoles of ss mutagenic nucleobase and 250 µl of PEG solution are gently but thoroughly mixed. After 20 min. incubation at room temperature, 5 mL cold 0.275 M $Ca(NO_3)_2$ are added dropwise. The protoplast suspension is centrifuged for 10 min at 85×g at 4° C. The supernatant is discarded and the protoplast pellet carefully resuspended in 1.25 mL $T_0$ culture medium supplemented with 50 µg·$mL^{-1}$ cefotaxime and 50 µg·$mL^{-1}$ vancomycin. ss mutagenic nucleobase culture medium contained (per liter, pH 5.7) 950 mg $KNO_3$, 825 mg $NH_4NO_3$, 220 mg $CaCl_2.2H_2O$, 185 mg $MgSO_4.7H_2O$, 85 mg $KH_2PO_4$, 27.85 mg $FeSO_4.7H_2O$, 37.25 mg $Na_2EDTA.2H_2O$, the micronutrients according to Heller's medium (Heller, R., *Ann Sci Nat Bot Biol Veg* 14: 1-223, 1953), vitamins according to Morel and Wetmore's medium (Morel, G. and R. H. Wetmore, *Amer. J. Bot.* 38: 138-40, 1951), 2% (w/v) sucrose, 3 mg naphthalene acetic acid, 1 mg 6-benzylaminopurine and a quantity of mannitol to bring the osmolality to 540 mOsm·kg$^{-1}$.

The suspension is transferred to a 35 mm Petri dish. An equal volume of $T_0$ agarose medium is added and gently mixed. Samples are incubated at 25° C. in the dark and further cultivated as described below.

Electroporation

The protoplasts are centrifuged at 85×g for 10 minutes at 5° C. The supernatant is discarded and the pellet resuspended in ice-cold electroporation buffer consisting of 10 mM HEPES, 80 mM NaCl, 0.04 mM CaCl$_2$, 0.4M mannitol, pH 5.7 adjusted to 540 mOsm·Kg$^{-1}$ with mannitol to a final concentration of 10$^6$ mL$^{-1}$. Protoplasts are kept on ice throughout the entire procedure. To a 0.4 cm wide electroporation cuvette, 4.5 nmoles ss mutagenic nucleobase and 700 µL of protoplast suspension are added. A single exponential decay pulse is delivered to the cell suspension using a Biorad GenePulser XCell electroporation system equipped with a PC and CE module according to the following parameters:

| Field strength | 500 V · cm-1 |
| Capacitance | 950 µF |

Under these conditions, the sample resistance is approximately 30 ohms and the resulting time constant approximately 30 ms. These parameters were selected as the parameters giving the highest level of transient expression of GFP in tobacco protoplasts, 24 hrs after electroporation. After pulsing, protoplasts are allowed to recover in the cuvette at room temperature for 30 min. The protoplasts are then recovered in 1 mL $T_0$ culture medium and transferred to a 10 mL tube. The cuvette is washed with an additional 5 mL $T_0$ culture medium which is pooled with the protoplast suspension. After thorough but gentle mixing, 50 µg·mL$^{-1}$ cefotaxime and 50 µg·mL$^{-1}$ vancomycin are added, and 1.25 mL of the protoplast suspension is transferred to a 35 mm Petri dish. An equal volume of $T_0$ agarose medium is added and the mixture is gently homogenized. Samples are incubated at 25° C. in the dark and further cultivated as described below.

Protoplast Cultivation

After 10 days of cultivation, the agarose slab is cut into 6 equal parts and transferred to a Petri dish containing 22.5 mL MAP1AO medium supplemented with 20 nM chlorsulfuron. This medium consisted of (per liter, pH 5.7) 950 mg KNO$_3$, 825 mg NH$_4$NO$_3$, 220 mg CaCl$_2$.2H$_2$O, 185 mg MgSO$_4$.7H$_2$O, 85 mg KH$_2$PO$_4$, 27.85 mg FeSO$_4$.7H$_2$O, 37.25 mg Na$_2$EDTA.2H$_2$O, the micro-nutrients according to Murashige and Skoog's medium (Murashige, T. and Skoog, F., Physiologia Plantarum, 15: 473-497, 1962) at one tenth of the original concentration, vitamins according to Morel and Wetmore's medium (Morel, G. and R. H. Wetmore, Amer. J. Bot. 38: 138-40, 1951), 6 mg pyruvate, 12 mg each of malic acid, fumaric acid and citric acid, 3% (w/v) sucrose, 6% (w/v) mannitol, 0.03 mg naphthalene acetic acid and 0.1 mg 6-benzylaminopurine. Samples are incubated at 25° C. in low light for 6-8 weeks. Growing calli are then transferred to MAP1 medium and allowed to develop for another 2-3 weeks. MAP$_1$ medium has the same composition as MAP$_1$AO medium, with however 3% (w/v) mannitol instead of 6%, and 46.2 mg·l$^{-1}$ histidine (pH 5.7). It was solidified with 0.8% (w/v) Difco agar. Calli are then transferred to RP medium using sterile forceps. RP medium consisted of (per liter, pH 5.7) 273 mg KNO$_3$, 416 mg Ca(NO$_3$)$_2$.4H$_2$O, 392 mg Mg(NO$_3$)$_2$.6H$_2$O, 57 mg MgSO$_4$.7H$_2$O, 233 mg (NH$_4$)$_2$SO$_4$, 271 mg KH$_2$PO$_4$, 27.85 mg FeSO$_4$.7H$_2$O, 37.25 mg Na$_2$EDTA.2H$_2$O, the micro-nutrients according to Murashige and Skoog's medium at one fifth of the published concentration, vitamins according to Morel and Wetmore's medium (Morel, G. and R. H. Wetmore, Amer. J. Bot. 38: 138-40, 1951), 0.05% (w/v) sucrose, 1.8% (w/v) mannitol, 0.25 mg zeatin and 41 nM chlorsulfuron, and is solidified with 0.8% (w/v) Difco agar. Mature shoots are transferred to rooting medium after 2-3 weeks.

Ss Mutagenic Nucleobases

All ss mutagenic nucleobase were synthesized by Eurogentec (Seraing, Belgium), purified by reverse phase HPLC and resuspended into sterile milliQ water. Prior to use, ss mutagenic nucleobase were heated up to 95° C. for 5 min. ss mutagenic nucleobase 06Q262 was designed to introduce a single mismatch (nucleotide underlined) in the tobacco ALS gene (accession number X07644) at codon position P194 which would result in a CCA to CAA (P194Q) conversion. The 06Q261 ss mutagenic nucleobase is the exact match to the tobacco ALS gene sequence and serves as negative control. The 06Q263 ss mutagenic nucleobase consists of a random combination of 40 nucleotides and serves as negative control.

[SEQ ID 1]
06Q261
5' TCAGTACCTATCATCCTACGTTGCACTTGACCTGTTATAG

[SEQ ID 2]
06Q262
5' TCAGTACCTATCATCCTACGT<u>T</u>GCACTTGACCTGTTATAG

[SEQ ID 3]
06Q263
5' ATCGATCGATCGATCGATCGATCGATCGATCGATCGATCG

Protoplast Survival Per Treatment

Protoplast survival after both PEG transformation and electroporation is assessed by esterase activity using the fluorescent vital dye fluorescein diacetate (FDA), 24 hrs after transformation. Two µL of a 5 mg·mL$^{-1}$ stock FDA in acetone are added to 1 mL of transformed protoplasts. The proportion of fluorescing protoplasts in the entire population is counted with a haemocytometer. Observations are carried out with a Nikon Eclipse E600 upright epifluorescence microscope equipped with a GFP LP (EX480/40, DM505, BA510) filter set. Excitation is provided by a 100 W super high pressure mercury lamp. Images are acquired using a DS-2MBWc CCD camera connected to a DS-U1 controller attached to a PC running the NIS Element image acquisition/analysis software.

Results

A summary of the transformation results using both PEG transformation and electroporation is presented in table 1. Using PEG transformation the protoplast survival rate is significantly higher compared to electroporation. The nature of electroporation itself is more detrimental to protoplasts survival than PEG transformation, resulting in a much higher recovery/survival rate as well as a higher targeted mutagenesis efficiency. The targeted mutagenesis efficiency is scored after incubation of the protoplasts in the presence of chlorsulfuron.

TABLE 1

Comparison of PEG transformation and electroporation with respect to protoplast survival rates.

| Mutagenic nucleobase | PEG treatment Survival** (%) | Electroporation Survival** (%) |
|---|---|---|
| 06Q261 | 83.5 ± 1.8 | 65.9 ± 2.2 |
| 06Q262 | 82.6 ± 2.1 | 66.3 ± 2.6 |
| 06Q263 | 83.8 ± 2.6 | 64.7 ± 3.1 |

*expressed as the percentage of fluorescing protoplasts after FDA staining in the recovered population of protoplasts.
Results are the average of 3 independent replicates ± SD.

PCR Amplification of ALS and Sequencing

DNA is isolated from chlorsulfuron resistant tobacco microcolonies using the DNeasy kit (Qiagen), and used as a template in a PCR reaction. Conversions of the targeted codons in the tobacco ALS gene are detected using the primers 5'GGTCAAGTGCCACGTAGGAT [SEQ ID 4] & 5'GGGTGCTTCACTTTCTGCTC [SEQ ID 5] that amplify a 776 bp fragment of this gene, including codon 194. Nucleotide conversion in the herbicide resistant tobacco callus is confirmed by cloning the PCR products into pCR2.1::TOPO (Invitrogen) and sequencing individual plasmids. Tobacco contains 2 alleles of ALS (SurA and SurB). Nucleotide conversion at the P194 codon of either of these loci is sufficient to confer resistance to chlorsulfuron. As tobacco is an allotetraploid species, there are eight possible targets in tobacco at which TNE may have occurred. In line with this, it was necessary to sequence >10 plasmid clones containing the PCR product to detect one with a CCA to CAA conversion. This suggests that in each resistant callus only 1 out of the 8 ALS alleles had undergone a targeted mutagenesis mediated nucleotide conversion. For all the calli produced in this study, we observed the expected CCA to CAA nucleotide conversion.

The invention claimed is:

1. A method for the production of a plant callus, plant shoot, or plant comprising an alteration in a genomic DNA sequence, wherein the method comprises the steps of:
   a) transforming plant cell protoplasts by treating the plant cell protoplasts with polyethylene glycol (PEG) and a donor single-stranded (ss) mutagenic nucleobase that comprises at least one mismatch with respect to the genomic DNA sequence to be altered, wherein the ss mutagenic nucleobase has a length of between 10-60 nucleotides;
   b) cultivating the treated protoplasts of step a); and
   c) regenerating the plant callus, plant shoot, or plant comprising the alteration in a genomic DNA sequence from the treated protoplasts,
   wherein the PEG transformation of step a) results in a significantly higher protoplast survival rate and targeted mutagenesis efficiency compared to electroporation and biolistics.

2. The method according to claim 1, wherein the ss mutagenic nucleobase comprises Locked Nucleic Acid (LNA) substitutions that are at least one nucleotide removed from the mismatch.

3. The method according to claim 2, wherein the ss mutagenic nucleobase comprises two LNAs located at least one nucleotide removed from either side of the mismatch.

4. The method according to claim 2, wherein the LNA substitutions are at least 3 nucleotides removed from the 5' and 3' ends of the ss mutagenic nucleobase.

5. The method according to claim 2, wherein the LNA substitutions are at least 4 nucleotides removed from the 5' and 3' ends of the ss mutagenic nucleobase.

6. The method according to claim 2, wherein the LNA substitutions are at least 5 nucleotides removed from the 5' and 3' ends of the ss mutagenic nucleobase.

7. The method according to claim 1, wherein the ss mutagenic nucleobase comprises propyne substitutions.

8. The method according to claim 1, wherein the ss mutagenic nucleobase is conjugated to a nuclear localization signal.

9. The method according to claim 1, wherein the donor ss mutagenic nucleobase comprises one mismatch with respect to the genomic DNA sequence to be altered.

10. The method according to claim 1, wherein the survival efficiency of the plant cell protoplast is greater than 90%.

* * * * *